(12) United States Patent
Jones

(10) Patent No.: US 8,702,673 B1
(45) Date of Patent: Apr. 22, 2014

(54) DISPOSABLE DIAPER OR INCONTINENCE UNDERGARMENT

(76) Inventor: Wanda F. Jones, Oakland, CA (US)

(*) Notice: Subject to any disclaimer, the term of this patent is extended or adjusted under 35 U.S.C. 154(b) by 431 days.

(21) Appl. No.: 13/116,951

(22) Filed: May 26, 2011

(51) Int. Cl.
*A61F 13/49* (2006.01)

(52) U.S. Cl.
USPC .......................................... 604/393; 604/386

(58) Field of Classification Search
USPC .................................................. 604/395, 389
See application file for complete search history.

(56) References Cited

U.S. PATENT DOCUMENTS

| | | | |
|---|---|---|---|
| 2,606,558 A | 8/1952 | Kennette | |
| 4,496,360 A | 1/1985 | Joffe et al. | |
| 5,217,447 A | 6/1993 | Gagnon | |
| 5,613,964 A * | 3/1997 | Grenier | 604/385.01 |
| 5,720,738 A | 2/1998 | Clark | |
| 5,910,137 A | 6/1999 | Clark et al. | |
| 6,045,543 A | 4/2000 | Pozniak et al. | |
| D436,400 S | 1/2001 | Klecker | |
| 6,652,498 B1 * | 11/2003 | Glasgow et al. | 604/385.01 |
| 6,840,926 B2 | 1/2005 | Nukina et al. | |
| 7,553,303 B2 * | 6/2009 | Speak | 604/385.14 |
| 2002/0143316 A1 | 10/2002 | Sherrod et al. | |
| 2003/0163105 A1 | 8/2003 | Tears et al. | |
| 2003/0225386 A1 | 12/2003 | Rodriguez | |
| 2004/0039361 A1 | 2/2004 | LaVon et al. | |
| 2004/0122401 A1 | 6/2004 | Van Gompel et al. | |
| 2005/0133387 A1 * | 6/2005 | Cohen et al. | 206/233 |
| 2010/0100068 A1 * | 4/2010 | Rodriguez et al. | 604/385.23 |

* cited by examiner

*Primary Examiner* — Susan Su

(57) ABSTRACT

A novel diaper, or other protective undergarment, is disclosed where the undergarment includes multiple absorbent layers that can be individually deployed once a first layer has been wetted or soiled. Each absorbent layer protects against the leakage of bodily fluids both laterally and vertically and once each of such layers is wetted or soiled, it can be removed from the undergarment thereby exposing a ready and dry second layer.

2 Claims, 4 Drawing Sheets

DISPOSABLE DIAPER OR INCONTINENCE UNDERGARMENT

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to disposable diapers, incontinence undergarments and similar articles. More specifically, the present invention relates to a dual-layered protective undergarment, such as a disposable diaper, where a first layer can be removed after it has been soiled leaving a second layer readied for use, Parents are all too familiar with the problems associated with diapers. It seems that if it's possible for an infant to go through all the diapers that one has packed, it will happen. And the disposable diaper, which is the most prevalent form of diaper in use today, is not a condensed product that stores easily. There is a "bulk" factor involved with disposable diapers that limits the number that a parent may reasonably carry around when shopping, or traveling, or when just running around doing errands. Certainly there have been aides for the parents that help to manage the diaper and baby care situations, such as storage bags that allow one to carry a number of diaper products along with formula and other supplies. Still, the total number of diapers remains limited and the potential for running low on diaper supplies is a real possibility at times.

In addition to diapers, the same issues hold true for other types of undergarments. Specifically, older persons do use undergarments that resemble disposable diapers for incontinence and other maladies. These undergarments generally have the same type of construction and use the same components albeit sized differently for an adult body. The benefits of the present invention apply equally to these types of products and any others that have similar characteristics.

There have been attempts in the prior art to improve the convenience and function of disposable diapers and similar products. For instance, in U.S. Patent Application No. 2004/0122401 A1 (Van Gompel, et al) teaches the use of a disposable undergarment with a separately detachable crotch area. The crotch portion is a supplemental absorbent and is used to augment the performance of undergarment in providing protection. In U.S. Pat. No. 6,840,926 B2 (Nukina, et al) a feminine hygienic pad is disclosed that includes multiple absorbent layers that can be exposed sequentially. The hygienic pad is directed for a certain use, however, that is less rigorous than the conditions experienced in applications such as a disposable diaper. Once soiled, the first exposed layer in the Nukina invention can be removed thereby exposing a next layer of absorbent protection. Similarly, in U.S. Pat. No. 5,910,137 (Clark, et al) a multilayered absorbent pad is disclosed for use as a feminine hygiene product. Each absorbent layer is segregate and once soiled; a layer can be removed to expose a new unused layer.

A disposable diaper is shown in U.S. Pat. No. 5,217,447 (Gagnon) where the invention provides for a reusable inner liner that can be used to extend the performance of the diaper product. The reusable liner is washable and can be reinserted into the crotch portion of the disposable diaper as can readily be seen and appreciated in the drawings. In this instance, the reusable liner merely provides additional absorbency and does not operate to allow multiple uses of a single disposable diaper type product. The objective is to reduce the amount of waste being disposed rather then extending the usage of the diaper type product.

In U.S. Pat. No. 5,720,738 (Clark) a feminine hygiene product is disclosed that includes multiple absorbent layers that are scaled laterally to prevent leakage from one layer to the next. The individual absorbent layers are subject to removal once soiled, but as was discussed above, the nature of the use of this product is different from the considerations that factor into a diaper or similar type of protective undergarment Lastly. U.S. Design Pat. No. D436,400 (Klecker) reveals a reusable diaper that appears to include an elastic rim and tab type fasteners.

The prior art has advanced the field of disposable diapers and feminine hygiene products although there still remain some longstanding problems. For instance, the need still exists for a protective undergarment with multiple and sequentially accessible absorbent layers that are capable of absorbing a substantial quantity of bodily waste products, e.g., urine and feces. The usual amount of elimination that is produced by an infant or an adult greatly exceeds that as might be anticipated for feminine hygiene products and typically occurs in one instance rather than the incremental accumulation that occurs in conjunction with feminine hygiene products. In addition, the need for an absorbent undergarment of the type exemplified by the present invention is shown by the lack of a diaper or adult protective undergarment that provides against segregate lateral and vertical leakage from multiple absorbent layers. This feature is important in maintaining those absorbent layers that are not in use in a dry and ready state and it prevents the exiting of bodily fluids from the edges of the undergarment.

In addition, there has been a long felt need for a protective undergarment that has multiple absorbent layers that is able to be packaged and stored in a convenient fashion. Further, there has been a long felt need for protective undergarments that have can assist the parent or user in finding tabs or snaps in darkened conditions. These and other problems that have been known have been resolved with the advent of the present invention as will be shown in the drawings and in the discussion below.

SUMMARY OF THE INVENTION

A novel protective undergarment is disclosed with a rim portion, a front and a rear, a crotch portion, formable into an undergarment that has leg openings and finable about the hip area of a user such as an infant or an adult. The undergarment further includes multiple absorbent layers that are segregate and which are maintained in a dry and ready state until they are deployed for use. A first absorbent layer may be exposed for use and when its capacity for retaining bodily fluids has been reached. it is removed and a next absorbent layer is exposed, repeating in sequential fashion until the absorbent layers are fully consumed.

The undergarment of the present invention also includes dams associated with each of the absorbent layers for protecting against lateral leakage and the loss of bodily fluids to the exterior of the protective undergarment. Each absorbent layer also includes an interface seal for the prevention of vertical leakage of bodily fluids in order to maintain any absorbent layer oriented below an absorbent layer in use in a dry and ready state.

Lastly, the protective undergarment of the present invention includes self illuminated aides comprising fluorescent fasteners that allow the user, parent or guardian the ability to see the fasteners under darkened conditions. In addition, the protective undergarment may be supplied with whimsical or decorative symbols that are fluorescent as well, which may provide a source of amusement for the wearer of the undergarment and which may also provide a means for a parent or guardian to locate the wearer of the undergarment under darkened conditions.

These and other attributes and benefits of the present invention will be disclosed in more detail below.

DETAILED DESCRIPTION OF THE PREFERRED EMBODIMENTS

Figure 1:
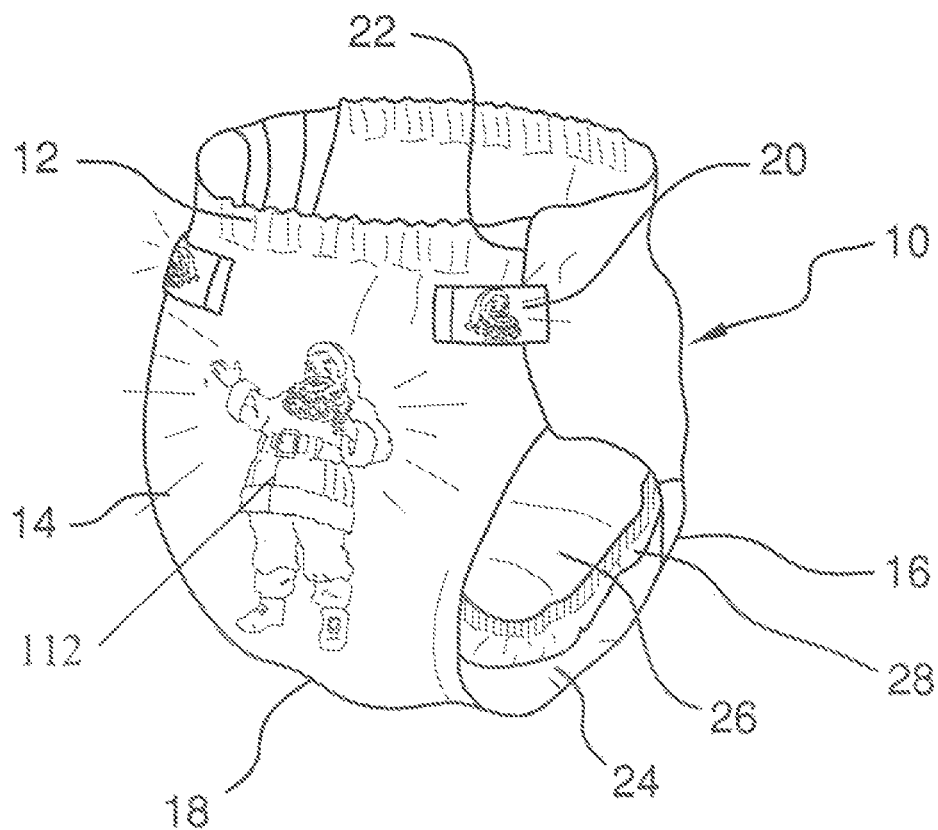
FIG. 1 is an isometric view of a prior art protective undergarment which is represented as a disposable diaper in this instance.

Situations arise when the need for a protective undergarment is required, Most commonly this occurs in the case of newborns and infants who have been typically been bundled with cloth (cotton) diapers. In years past, cloth diapers were accepted as the product of choice since they were inexpensive, could be reused, and they were highly absorbent. Still, cloth diapers lacked complete controls of the bodily fluids that a newborn or infant might eliminate. To this end, plastic overpants where developed to encompass the cloth diapers. The plastic overpants had elastic waistbands and elastic leg openings and helped to contain the fluids and prevent a wet or soiled cloth diaper from contacting other clothes or linens.

Following years of experience in using cloth diapers, parents were introduced to disposable diapers. Constructed in a manner analogous to the cloth diaper and plastic overpants, the disposable diaper sported an absorbent inner layer that was bonded to a plastic outer layer that served as a liner to prevent bodily fluids from leaching to the exterior. Disposable diapers were literally disposable in the sense that early versions were promoted as being flushable down a toilet or similar, however. this practice has been discouraged for a number of reasons including the potential for clogging drain and sewer lines and for unduly loading the waste treatment facilities. The disposable diaper is disposed of through solid waste channels which is still a matter of great convenience to the parent. The use of disposable diapers has grown tremendously and they are now the preferred product of choice when it comes to bundling a new born or infant.

Notwithstanding the popularity of disposable diapers, they clearly have some deficits that render them difficult at times. For one, they have a bulk that makes them difficult to store easily. Especially when one desires or needs to carry more than one diaper at a time. For a parent who is traveling with an infant, it becomes a major nuisance to have to lug a number of disposable diapers around. And as will occur at times, the parent may forget to bring along a sufficient quantity of diapers (or a number of them may be needed unexpectedly) resulting in a situation where the infant is left wearing a wet or soiled diaper until the situation can be handled. This is obviously a less than desirable effect and when it occurs it may mean the cessation of a trip, a return to home. or other diversion from the plans that had been made by the parent.

Much of the same attributes apply to an equally potent application. Protective undergarments are used by adults and are very similar in design and structure as the diapers discussed above. In fact, a number of disposable undergarments of this type are actively marketed and are purchased in substantial quantities. The same subset of problems are evident in these protective undergarments and for the purposes of this application, the discussion about the disposable diapers applies equally to all such protective undergarments.

Figure 2:
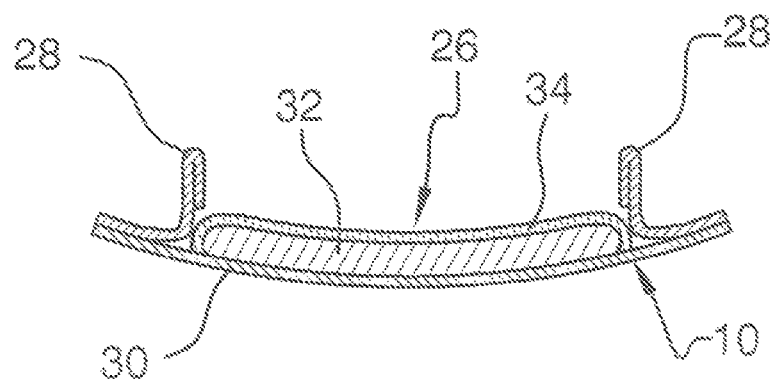
FIG. 2 is a cross section view of a crotch portion of the protective undergarment of FIG. 1, showing the single absorbent layer that is supplied therein.

Turning now to the drawings, FIGS. 1 and 2 disclose a prior art disposable diaper (protective undergarment) 10 that includes a rim 12, a front 14, a rear 16, a crotch portion 18. The disposable diaper 10 can be fastened by means of the adhesive fastener tab 20 located near the scam 22. The disposable diaper 10 further includes the leg opening(s) 24, the absorbent layer 26 and the dam 28. More detail of the absorbent layer 26 can be seen in FIG. 2 where the plastic liner 30 is shown in conjunction with the absorbent layer interior 32 and the absorbent layer exterior 34. The absorbent layer exterior 34 is typically a light weight and thin plastic liner that encompasses the absorbent layer interior 32 and which has been made highly permeable with a multitude of holes. The absorbent layer interior 32 is the actual absorbing component and may be made from cotton and synthetic constituents that optimally absorb a large quantity of bodily fluids in a short period of time. The purpose of the absorbent layer exterior 34 appears to be to retain the absorbent layer interior 32 and keep it intact.

The prior art disposable diaper is typically a single-use product. Once the diaper has been wetted or soiled, the impermeable plastic liner, which is integrally formed as part of the exterior of the diaper itself, prevents any leakage through the body of the diaper. The dam similarly is formed from a plastic that is impermeable to water and/or bodily fluids, and prevents leakage laterally from the body of the diaper and retains bodily fluids within the absorbent layer to the extent possible. Being single-use, the disposable diaper is thrown away once it has performed its function.

Figure 3:
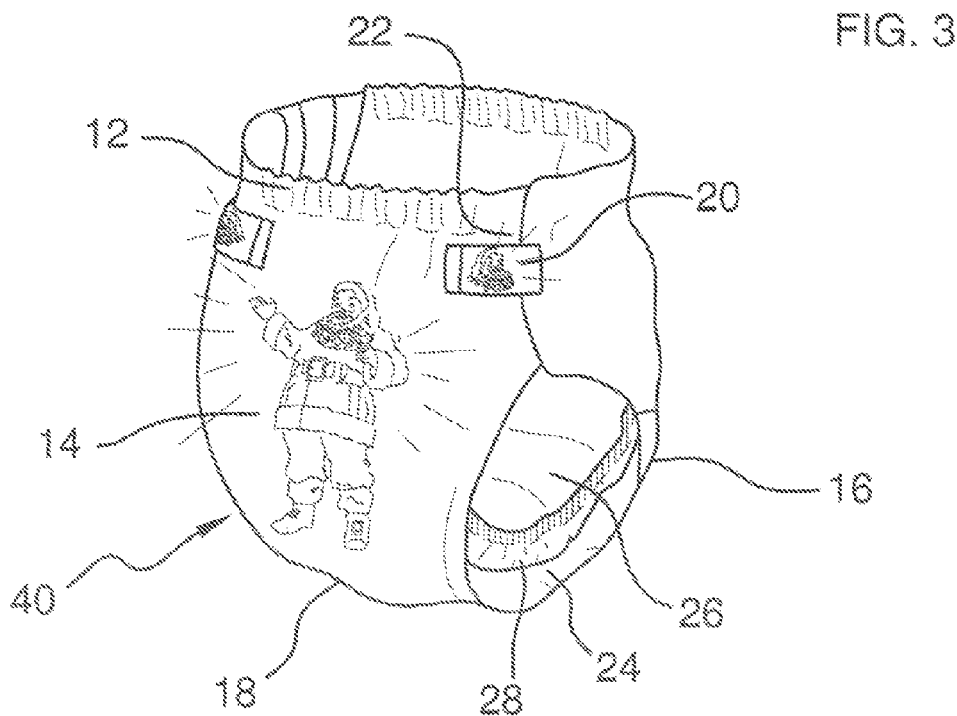
FIG. 3 is an isometric view of a protective undergarment of the present invention with a tab type fastener.
Figure 4:
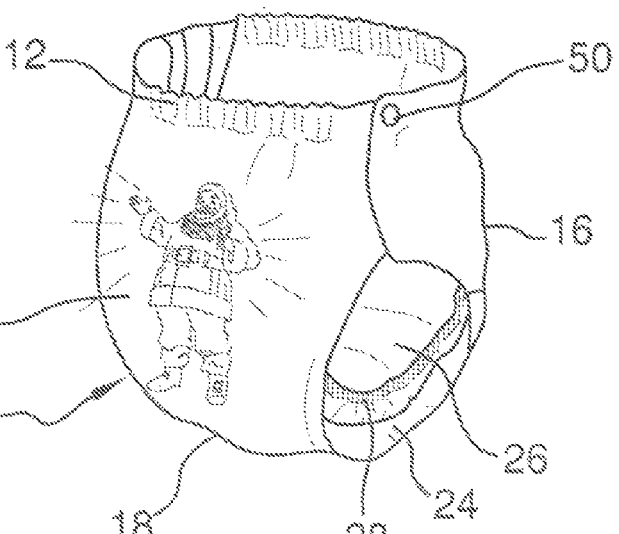
FIG. 4 is an isometric view of a protective undergarment of an alternate version of the present invention with a snap type fastener.
Figure 5:
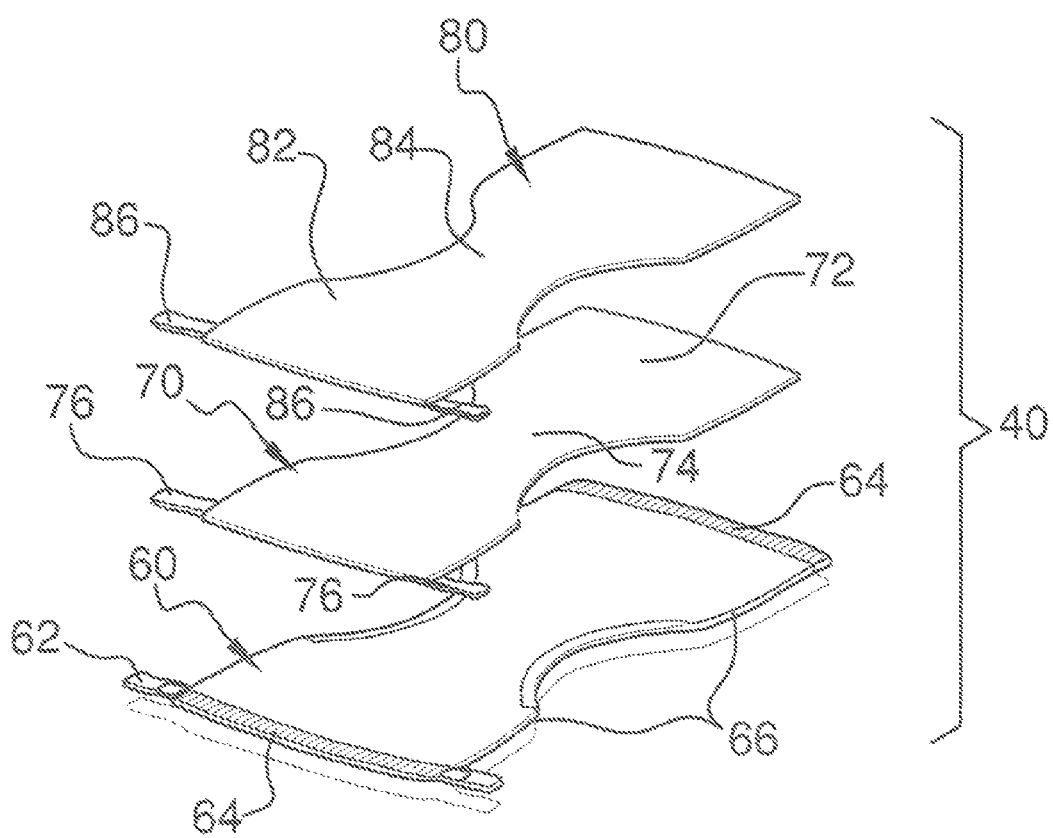
FIG. 5 is an exploded isometric view of a protective undergarment of the present invention showing the multiple absorbent layers.
Figure 6:
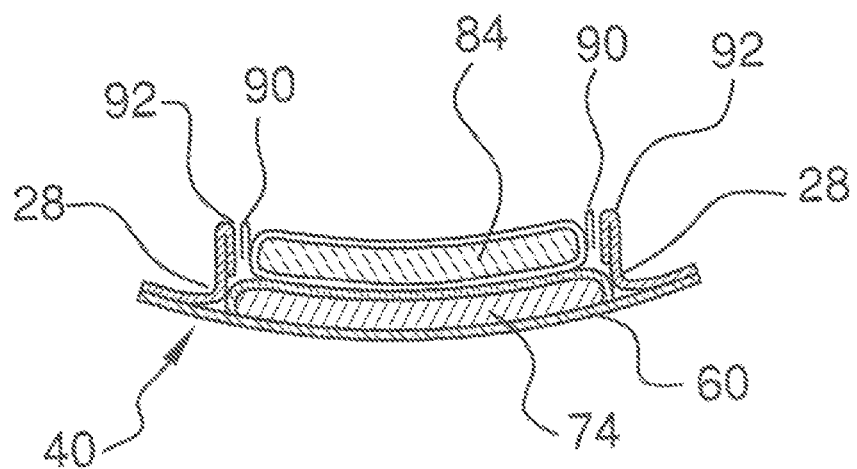
FIG. 6 is a cross sectional side view of the crotch portion of the protective undergarment shown in FIG. 5.
Figure 7:
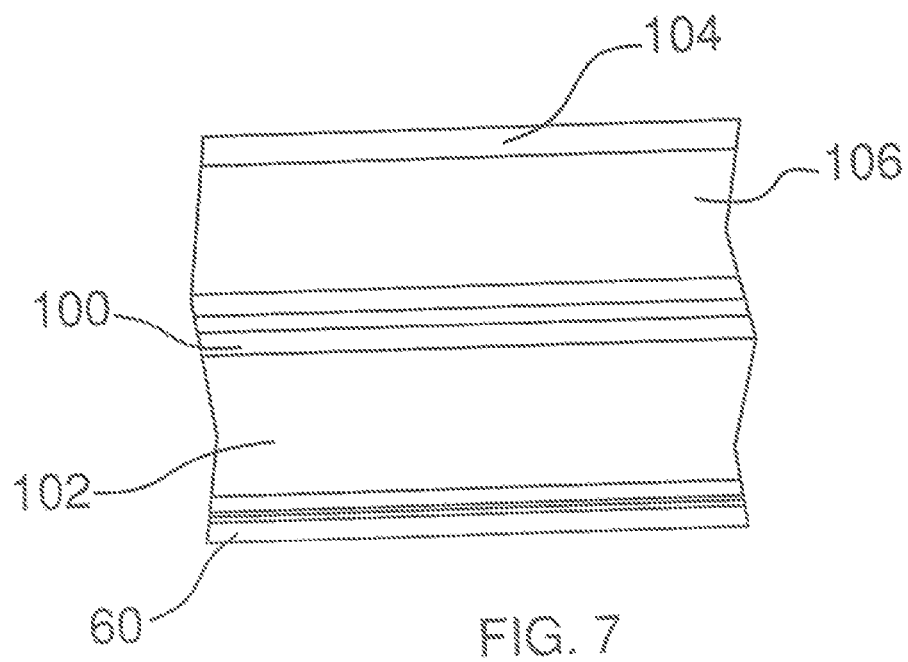
FIG. 7 is a detailed cross sectional view of the center of the crotch portion of FIG. 6.

The protective undergarment of the present invention is disclosed in the rest of the drawings and commencing with FIGS. 3,4 and 5, it can be seen that a disposable diaper 40 includes a rim 12, a front 14, a rear 16, a crotch portion 18. As shown in FIG. 3, the disposable diaper 40 can be fastened by means of the adhesive fastener tab 20 located near the seam 22. The disposable diaper 40 further includes the leg opening(s) 24, the absorbent layer 26 and the dam 28. In FIG. 4, the disposable diaper 40 can be fastened by the snap 50 in lieu of the adhesive fastener tab 20. FIG. 5 reveals the functional aspects of the present invention where the disposable diaper 40 includes a plastic liner 60, tab liners 62, elastic 64, and edging 66. The second absorbent layer 70 is shown with the associated absorbent 72, the second absorbent crotch portion 74 and the second absorbent adhesive fastener tabs 76. Above the second absorbent layer 70 is the first absorbent layer 80 with the associated absorbent 82, the first absorbent crotch portion 84 and the first absorbent adhesive fastener tabs 86.

in FIGS. 6 and 7, aspects of the crotch portions of the disposable diaper 40 of the present invention are shown, with the second absorbent layer crotch portion 74 and the first absorbent layer crotch portion 84 are seen in detailed cross sectional views. Specifically, FIG. 6 shows the relationship between the first and second absorbent layers relative to the plastic liner 60, including a view of the first absorbent layer dam 90 and the interface 92. In FIG. 7, the second absorbent layer exterior 100 is shown in conjunction with the second absorbent layer interior 102. Similarly, the first absorbent layer exterior 104 is shown in conjunction with the first absorbent layer interior 106.

In use, the disposable diaper of the present invention is used in an identical manner as the conventional prior art disposable diaper. The presence of the multiple layers of absorbent do not normally cause any outward difference and functionality of the diaper product remains much the same. However, once the diaper has been wetted or soiled as would be anticipated during use, the first absorbent layer takes up the bodily fluids and performs the absorbing function to keep the infant as dry as is feasible. As would normally be the case, the parent will notice the diaper has become wetted or soiled and may then proceed to open the diaper by undoing either the adhesive fastener tabs emanating from the first absorbent layer. The parent can then pull the first absorbent layer away from the second absorbent layer, typically at the adhesive fastener tabs, and cause the whole first absorbent layer to be removed. This happens because the first absorbent layer and the second absorbent layer are not really affixed to each other but may be held in place by the frictional engagement and/or by the use of a weak adhesive that nominally keeps the two layers held together. In any event, the first absorbent layer can be lifted off the second absorbent layer, and where the first absorbent layer can then be disposed of, the second absorbent layer is now exposed and is ready for use. The thickness of the absorbent layers can be adjusted for additional retention as may be desired, in fact the product may be offered for differing levels of absorbency allowing the consumer to decide which level of protection may be needed.

The second absorbent layer has essentially been protected from wetting and/or soiling by the interface which may be adhered to the first absorbent layer. The interface operates like a liner and is impermeable to the bodily fluids that may contact it when the first absorbent layer has become wetted or soiled. In addition, the first absorbent layer dam is attached to the interface and extends alone the sides of the first absorbent layer. This first absorbent layer dam prevents the lateral leakage of bodily fluids from the first absorbent layer which not only prevents the loss of such bodily fluids from the diaper but it also prevent the second absorbent layer from becoming wetted and/or soiled. Thus the second absorbent layer remains in a dry and ready state until it is needed. Thus the removal of the first absorbent layer serves to open the second absorbent layer which is then ready for use.

The diaper (or protective undergarment) of the present invention allows multiple uses within the same product This function assists in those situations where the diaper supply is nominal or where space is limited. The fact that both absorbent layers use the same plastic liner and related components, the size of the diaper product with multiple layers is able to be substantially smaller in bulk than would be the case if multiple diapers had to be used.

Unlike the prior art products, the present invention provides for protection of leakage laterally and vertically (being defined as leakage that would occur directly through the crotch portion of an absorbent layer). A differentiation may also be made with respect to the level of protection afforded male versus female applications. For instance, the crotch are in the male diaper product may be provided with extra absorbency and/or strength to accommodate a perceived need.

It is understood that the diaper of the present invention will be supplied as a one-piece construction as may be appreciated by the disclosure of the invention in FIG. 5. The front and the rear of the diaper can be brought together to form the diaper shape as shown in FIGS. 3 and 4 although this is usually done directly on the newborn or infant. The waist area, defined by the rim of the diaper, is adjustably fitted to the newborn or infant by overlapping the back portion of the diaper with the front portion, thus forming the seams on the sides of the diaper. The adhesive fastener tabs are activated by removing the protective plastic protector on the adhesive portions (not shown) the operation and assembly of which are well know in the art. The adhesive fastener tabs are strong enough to retain the rear of the diaper to the front and keep it from loosening up while being used on the infant.

One aspect of the present invention is the fact that each absorbent layer preferentially has its own set of adhesive fastener tabs that are bonded to the plastic liner tabs of the plastic liner. This allows each absorbent layer to utilize the benefits of the elastic that is supplied to the rim of the diaper and which assists in fitting the product to the newborn or the infant.

As alluded to above, the adhesive fastener tabs can be replaced with snaps. The snaps have the advantage of being fitted onto the plastic liner and not to each absorbent layer as is the case for the adhesive fastener tabs. Snaps are well known in the art and as such do not specifically comprise a part of the present invention except as use din combination with novel components of the present invention. Snaps do typically require two component parts, a male and a female which are alignable for fastening purposes.

An enhancement of the above embodiments may include an adhesive fastener tabs that can incorporate self-illuminating characters. The self illuminating characters 112 can also be deployed on the rim of the diaper product. The advantage is that these characters provide an indication of the diaper location when in darkened conditions. It often happens that a parent will have to change a diaper while in a traveling vehicle during nighttime conditions. There are other occasions when diaper changing may have to take place under low-light conditions. The usage of self-illuminating characters will help the parent to locate the fastener tabs or snaps under such conditions. The characters also provide, secondarily, a whimsical appearance as well and may be tailored to match the gender of the child, e.g., male character types for male infants, and female character types for female infants. The self illumination typically is the result of fluorescent components. The rim may also be provided as a glow-in-the-dark item on the diaper of the present invention.

As mentioned above, the present invention is not just limited to diaper type products. Adult protective undergarments would also benefit from the teachings herein. Any other application that reasonably contemplates the need for multiple absorbent layers could be considered as well and could include sports equipment where sweating produce the need to replace an absorbent layer in a helmet, or in the uniform of a participant.

Variations in the components or the number of layers are anticipated under the present invention as well. For instance, while two layers are shown as the preferred embodiment, more could be used so long as the functionality of the absorbent layers and the ability for the undergarment to be worn normally are not affected. Therefore no limitation on the scope of the invention is implied or intended as a result of the disclosures made within this specification.

I claim:

1. A multi-use protective undergarment for use by a person, fittable about the waist and around the legs of a person for the protective retention of bodily fluids, comprising:
   (a) a plastic liner having a tab liner, elastic, edging, and an interface disposed thereon, wherein the liner and the interface are impermeable to bodily fluids;
   (b) a nonremovable second absorbent layer having absorbent disposed therein, a second absorbent crotch portion and a second absorbent adhesive fastener tab disposed on the tab liner, wherein the interface surrounds edges of the second absorbent layer to laterally seal bodily fluids into the second absorbent layer; and
   (c) a removable first absorbent layer having absorbent disposed therein, a first absorbent crotch portion and a first absorbent adhesive fastener tab disposed on the second absorbent adhesive fastener tab and the tab liner, wherein the first absorbent layer comprises a dam disposed thereon, wherein the dam is impermeable to bodily fluids, wherein the dam surrounds edges of the first absorbent layer to laterally seal bodily fluids into the first absorbent layer;
   wherein the second absorbent layer is permanently disposed on a top surface of the plastic liner,
   wherein the first absorbent layer is disposed on but not attached to a top surface of the second absorbent layer,
   wherein the dam of the first absorbent layer contacts the interface for forming a seal at the edges;
   wherein the undergarment comprises a rim, a front, a rear, a crotch portion, and leg openings disposed thereon, wherein the undergarment comprises a fastener tab located near a seam for fastening the undergarment, wherein the fastener tab consists of the first absorbent adhesive fastener tab disposed on the second absorbent adhesive fastener tab together disposed on the tab liner, thereby attaching the liner, the second absorbent layer, and the first absorbent layer into an undergarment,
   wherein upon removal of the first absorbent layer, the second absorbent layer is exposed for use.

2. The undergarment of claim 1, wherein the undergarment further includes self-illuminated characters disposed thereon.

* * * * *